(12) United States Patent
Dilmanian et al.

(10) Patent No.: US 7,305,064 B2
(45) Date of Patent: *Dec. 4, 2007

(54) METHODS FOR ASSISTING RECOVERY OF DAMAGED BRAIN AND SPINAL CORD USING ARRAYS OF X-RAY MICROPLANAR BEAMS

(75) Inventors: F. Avraham Dilmanian, Yaphank, NY (US); John W. McDonald, III, Baltimore, MD (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/591,125

(22) Filed: Nov. 2, 2006

(65) Prior Publication Data

US 2007/0165778 A1 Jul. 19, 2007

Related U.S. Application Data

(63) Continuation of application No. 11/054,000, filed on Feb. 10, 2005, now Pat. No. 7,158,607.

(51) Int. Cl.
*A61N 5/10* (2006.01)
*G21K 5/00* (2006.01)

(52) U.S. Cl. .......................... 378/65; 378/64

(58) Field of Classification Search .................. 378/1, 378/2, 64, 65, 108
See application file for complete search history.

(56) References Cited

U.S. PATENT DOCUMENTS

| | | | | | |
|---|---|---|---|---|---|
| 5,168,516 | A | * | 12/1992 | Ito | 455/462 |
| 5,339,347 | A | * | 8/1994 | Slatkin et al. | 378/65 |
| 5,755,752 | A | * | 5/1998 | Segal | 607/89 |
| 6,033,431 | A | * | 3/2000 | Segal | 607/89 |
| 6,063,108 | A | * | 5/2000 | Salansky et al. | 607/89 |
| 6,494,900 | B1 | * | 12/2002 | Salansky et al. | 607/89 |
| 2004/0005027 | A1 | * | 1/2004 | Nafstadius | 378/65 |

* cited by examiner

*Primary Examiner*—Edward J. Glick
*Assistant Examiner*—Irakli Kiknadze
(74) *Attorney, Agent, or Firm*—Lori-Anne Neiger

(57) ABSTRACT

A method of assisting recovery of an injury site of brain or spinal cord injury includes providing a therapeutic dose of X-ray radiation to the injury site through an array of parallel microplanar beams. The dose at least temporarily removes regeneration inhibitors from the irradiated regions. Substantially unirradiated cells surviving between the microplanar beams migrate to the in-beam irradiated portion and assist in recovery. The dose may be administered in dose fractions over several sessions, separated in time, using angle-variable intersecting microbeam arrays (AVIMA). Additional doses may be administered by varying the orientation of the microplanar beams. The method may be enhanced by injecting stem cells into the injury site.

24 Claims, 4 Drawing Sheets

METHODS FOR ASSISTING RECOVERY OF DAMAGED BRAIN AND SPINAL CORD USING ARRAYS OF X-RAY MICROPLANAR BEAMS

CROSS-REFERENCE TO RELATED APPLICATIONS

This application is a continuation of U.S. application Ser. No. 11/054,000, filed on Feb. 10, 2005 now U.S. Pat. No. 7,158,607.

This invention was made with Government support under contract number DE-AC02-98CH10886, awarded by the U.S. Department of Energy. The Government has certain rights in the invention.

FIELD OF THE INVENTION

The present invention relates generally to methods for assisting recovery of damaged spinal cord and brain and more particularly to methods of using arrays of x-ray microplanar beams to assist recovery of damaged spinal cord and brain.

BACKGROUND OF THE INVENTION

An injury to a portion of the central nervous system (CNS), i.e., the spinal cord or brain, can not be healed by the same means used to treat tissue types such as bone, muscle, liver, the peripheral nervous system (PNS), and so on. An injured spinal cord, for example, does not heal and recover to become functional again, as other tissue types do. For example, severed axons at the injury site fail to reestablish synaptic connections, resulting in permanent loss of neural activity.

In addition, beginning over the first two weeks after injury, cellular changes are triggered that lead to the formation of scar tissue that acts as a barrier to prevent regeneration. For example, astrocytes, the neuroglial cells which normally provide structural support and protection to the neurons, transform into reactive astrocytes upon injury. These reactive astrocytes accumulate to form the bulk of a scar tissue that forms, which is referred to as a gliosis (or astrogliosis); and, at a later stage, as a glial scar. This gliotic tissue acts as a barrier to the reconnection of remaining uninjured tissue, including axons and neurons, and prevents regeneration of healthy neural tissue. Without regeneration and reconnection, there is no return to functionality.

Other processes that are related to the production of reactive astrocytes and may hamper the recovery are: a) production and dissipation at the injury site of axon-growth inhibiting molecules such as chondroitin-sulfate proteoglycans (CSPGs) and keratan-sulfate proteoglycans (KSPGs); and b) reaction of the immune system, commonly in the form of white blood cells (leukocytes) at the entrance to the injury site.

The barrier formed at the injury site consists of functional barriers or inhibitors, as well as physical barriers. For example, the astrogliosis layer that forms at the injury site, also called the junction (referring to the junction between healthy tissues), prevents the recovery of the set of systems required to restore function including formation of the microvasculature system. With the failure of early vascular recovery, catastrophic vascular collapse ensues leading to tissue cavitation and stroke-like events. The overall failure of repair of the microvasculature induces tissue collapse and a failure to bridge the junction between healthy tissues separated by the glial tissue or glial scar.

One of the only methods currently being researched to solve the problem is irradiation of the injury site with X-rays within two to three weeks after the occurrence of injury, as described, for example, in Kalderon, et al., "Structural Recovery in Lesioned Adult Mammalian Spinal Cord by X-Irradiation of the Lesion Site," Proc. Natl. Acad. Sci. USA, Vol. 93, pp. 11179-11184 (October 1996), or in Kalderon, at al., "Fractionated Radiation Facilitates Repair and Functional Motor Recovery after Spinal Cord Transection in Rat." Brain Res. Vol. 904, pp 199-207 (June 2001), both of which are incorporated herein by reference. Although the method has produced some encouraging results in laboratory animals, it has not been shown to produce substantial functional repair of the spinal cord.

Other methods have focused on limiting the functional expression of inhibitors or altering the microenvironment that prevents spontaneous regeneration. Yet others attempt to chemically ablate the inhibitory scar barrier. These methods are limited by the lack of non-invasive methods for delivery of the chemicals/compounds required to produce the effect. These methods also exhibit substantial negative "bystander" effects that are overall deleterious to the repair process, often exacerbating injury.

There is a need, therefore, for more successful, safe irradiation methods for assisting functional recovery of a damaged spinal cord or brain.

SUMMARY OF THE INVENTION

The present invention, which addresses the needs of the prior art, relates to a method for assisting recovery of acute or chronic injury to the brain or spinal cord by irradiating the injury site with array(s) of X-ray microplanar beams. The goal of the method of the present invention is to inhibit the formation of a scar barrier formed by injury to the spinal cord or brain, and simultaneously promote the regeneration of the damaged microvasculature and glial system to produce substantial functional recovery.

The present invention includes a method of assisting recovery of an injury site of an acute or chronic injury to a brain or spinal cord of a subject. The method includes irradiating the injury site with at least one array of microbeams. Each array includes at least two parallel, spatially distinct microbeams in an amount and in such a spatial arrangement to allow delivery of a therapeutic dose of X-ray radiation to the injury site.

The therapeutic dose preferably includes an in-beam in-depth dose in each microbeam substantially in a range from about 30 Gy to about 500 Gy.

Preferably, the method includes irradiating the injury site using a number n of angle-variable intersecting microbeam arrays ("AVIMA") delivered in different sessions, where each session is separated by a time interval. This method is referred to as "AVIMA with dose fractionation." After irradiating the injury site with one of the angle-variable intersecting microbeam arrays in one session, the remaining angle-variable intersecting microbeam arrays are preferably generated by repeatedly angularly displacing either an X-ray radiation source generating the arrays or the subject about an axis of rotation through a center of the injury site and additionally irradiating a number (n−1) times, after the time interval required between irradiating sessions, to generate the number n of angle-variable intersecting microbeam arrays. The axis of rotation is parallel to the at least two parallel, spatially distinct microbeams.

A pattern of radiation is generated such that the angle-variable intersecting arrays intersect substantially only within the injury site. In addition, adjacent angle-variable intersecting microbeam arrays are spatially separated by a displacement angle, which is preferably equal to θ/(n−1), wherein θ is predetermined by an angular access of an X-ray source generating the angle-variable intersecting microbeam arrays to the injury site.

The method also preferably includes angular displacement of either the source of the microbeam arrays or the subject by a non-zero integer multiple of the displacement angle between sessions. In other words, any temporal sequence of the angle-variable intersecting microbeam arrays may be used to irradiate the injury site.

The total angular spread θ defines the total separation between arrays, and, thus, encompasses the angle-variable intersecting microbeam arrays. In one embodiment, the angular spread is substantially in a range of about 130 degrees to about 150 degrees.

The present invention may also include generating a set of n angle-variable intersecting microbeam arrays, where each of the angle-variable intersecting arrays may be generated with the same, or a different irradiation orientation of the at least two parallel, spatially distinct microbeams (microplanar beams), where the possible irradiation orientations are either horizontal, vertical, or slanted (not horizontal or vertical).

In one embodiment, the set of n-angle-variable intersecting microbeam arrays are generated for one irradiation orientation, either horizontal, vertical, or slanted at a particular angle. The method may also include additionally generating a second number n of angle-variable intersecting microbeam arrays, using a different irradiation orientation of the microbeams for another n sessions. Each session is separated by the time interval. The different orientations may be generated by either repositioning the multislit collimator or changing to a different multislit collimator. As a result, the injury site is irradiated for a total number 2n of sessions. Preferably, the total number 2n of sessions ranges from three (3) to thirty (30) sessions.

The subject may be positioned for irradiation treatment in one of an upright position, a side-reclined, and a slanted position. The arrays are preferably centered around a zero-angle array that impinges on the patient's back at a 90 degree angle of incidence.

The method of irradiating the injury site with AVIMA may be implemented in sessions separated by the time interval of at least twelve (12) hours to about seven (7) days.

The array(s) of the present invention preferably include a center-to-center spacing between adjacent microbeams and a thickness of each of the at least two parallel, spatially distinct microbeams, wherein a ratio of the center-to-center spacing to the thickness is substantially in a range of about 4 to about 16.

In one embodiment, the method includes generating the X-ray radiation with an X-ray bremsstrahlung source. The microbeams in the array(s) generated with the bremsstrahlung source preferably have a thickness substantially in a range of about 0.1 millimeters (mm) to about 1.0 mm. Alternatively, the method may include generating synchrotron X-ray radiation, in which case, each of the at least two parallel, spatially distinct microbeams include a beam thickness substantially in a range of about 20 micrometers (μm) to about 100 μm.

In another embodiment, the thickness of the microbeams is substantially in a range of from about 0.02 mm (20 μm) to 1.0 mm.

The preferred X-ray radiation from a source generating the microbeam arrays has a filtered broad beam energy spectrum, with a half-power energy being substantially in a range from at least about 100 keV to about 250 keV.

In an additional embodiment of the method of the present invention, the method further includes delivering stem cells to the injury site.

The method may also include delivering the microbeam array(s) of the present invention to the injury site in a plurality of temporally discrete pulses of X-ray radiation, which are, in one embodiment, substantially synchronized with a physiomechanical cycle of the subject. Preferably, the physiomechanical cycle includes at least one of a cardiac cycle and a cardiopulmonary cycle.

As a result, the present invention provides a method for assisting recovery of acute or chronic brain injury to the brain or spinal cord.

DETAILED DESCRIPTION OF THE INVENTION

The present invention provides a method of assisting physiological, neurological, and functional recovery of a damaged spinal cord or brain by delivering a therapeutic dose of X-ray radiation to the injury site using microplanar X-ray beams. The method preferably inhibits or minimizes the formation of an astrogliotic or gliosis barrier at the site of injury and simultaneously promotes the regeneration and reconnection of axons. The in-beam therapeutic dose at the injury site, delivered by the microbeams, preferably operates to promote a less hostile environment in which the presence of growth inhibiting molecules and leukocytes is minimized and the recovery of the glial system and remyelination processes are encouraged.

Figure 1:
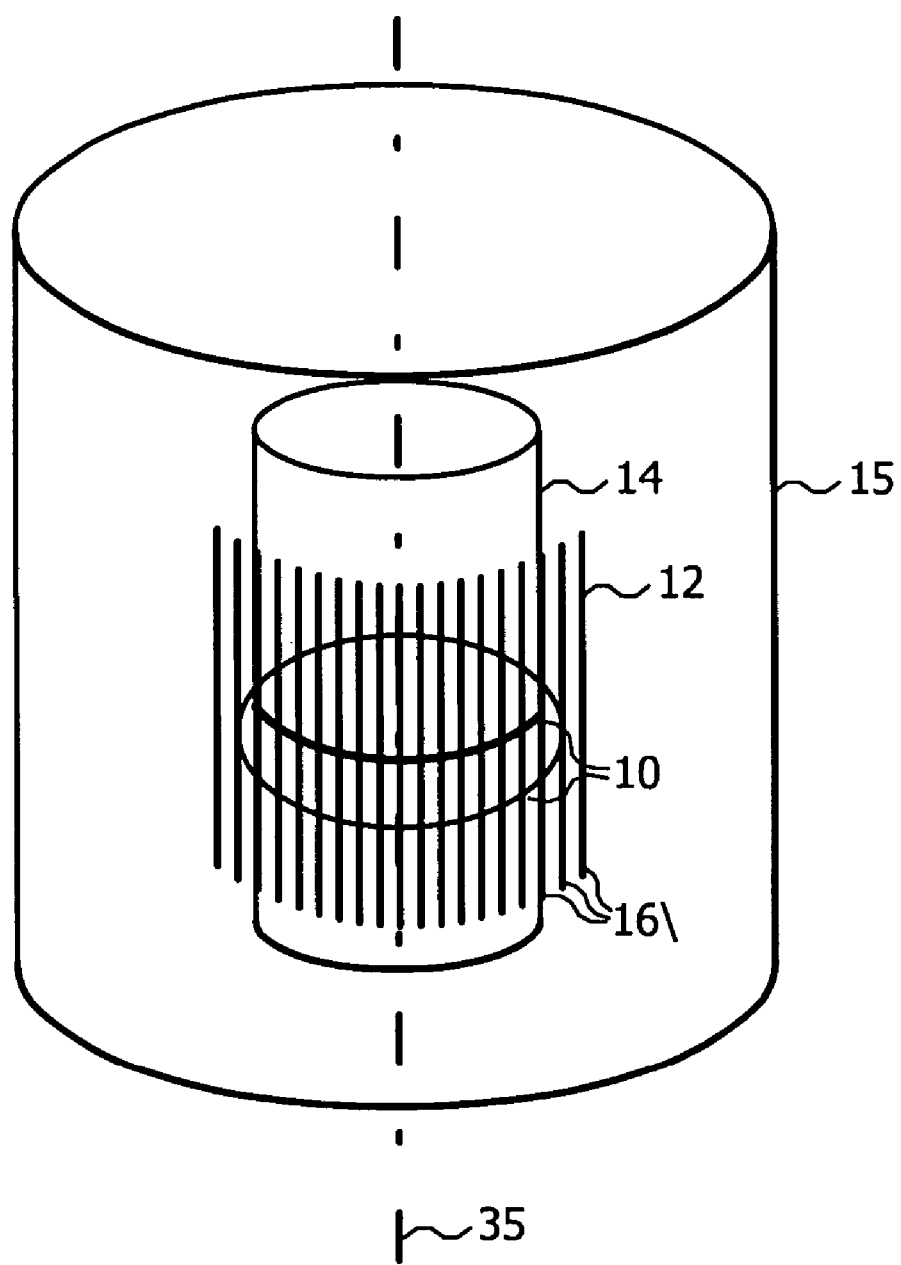
FIG. 1 is a schematic representation of the cross-section of a microbeam array of the present invention irradiating an injured spinal cord.

Referring to FIG. 1, the present invention provides a method of assisting functional recovery of a damaged spinal cord or brain by irradiating an entire area of spinal cord or brain damage, i.e., the injury site 10, with at least one array of microplanar beams 12 of X-ray radiation. The particular pattern of radiation formed by the microbeam irradiation at the injury site 10 preferably both inhibits the formation of a gliotic barrier formed by injury to the spinal cord or brain, and promotes the regeneration of the damaged microvasculature general system to produce substantial functional recovery. The method of the present invention preferably promotes this regeneration by encouraging a bridging of healthy tissue on opposite sides of the damaged area. This is accomplished preferably by reducing the concentration of reactive astrocytes and axon-growth inhibiting molecules such as condroitin-sulfate proteoglycans (CSPGs) and keratan-sulfate proteoglycans (KSPGs) and immune-response cells such as leukocytes, and promoting remyelination to produce substantial physiological, neurological, and functional recovery.

The use of microbeam arrays is known in the prior art for use in microbeam radiation therapy (MRT) as an experimental method for the treatment and ablation of tumors, as described, for example, in U.S. Pat. No. 5,339,347 to Slatkin et al., which is incorporated herein by reference. MRT differs from conventional radiation therapy by employing arrays of preferably parallel and planar microbeams of radiation (microplanar beams). The thickness of each microplanar beam is at least one order of magnitude smaller in thickness (or diameter if cylindrical rather than planar beams are used) than the smallest radiation beams in conventional clinical use. The entire width of the array, however, may still cover an area comparable to that covered using broad beam. The advantage over conventional broad beam radiation for tumor ablation and control is that the irradiated normal tissue in the path of the individual microbeams, which is often irreversibly damaged by conventional radiation therapy, is allowed to recover from any radiation injury by regeneration from the supportive cells surviving between the microbeams.

The Slatkin et al. patent discloses the segmentation of a broad beam of high energy X-ray into arrays of parallel microbeams (beams of thickness less than about 1 millimeter (mm)), and a method of using the microbeams to perform radiation therapy on tumors. The tumor receives a summed absorbed dose of radiation exceeding a maximum absorbed dose tolerable by the target tissue by crossing or intersecting microbeams at the target tissue. The irradiated in-beam normal tissue is exposed only to non-crossing beams. Normal tissue between the microbeams receives a summed absorbed dose of radiation, called a valley dose, less than the maximum tolerable dose; i.e., normal tissue in the valleys receives a nonlethal dose, leaving surviving supporting cells. The surviving cells migrate to the irradiated normal tissue in the path of the microbeam, allowing normal tissue in the path of the beam to recover from radiation injury.

The method of the present invention includes irradiating the injury site of an acute (injury site less than 20 days old) or chronic (more than 20 days old) injury to the spinal cord or brain with an array of microbeams, which are preferably parallel microplanar beams, instead of using a conventional, unsegmented broad beam, to assist recovery from the injury. The use of microbeam arrays for recovery of damaged spinal cord and brain takes advantage of the normal tissue-sparing characteristics offered by the geometry of microbeam arrays, described supra. The microbeam arrays allow the normal tissue, including that of the central nervous system (CNS) which encompasses the spinal cord, to recover almost completely from the damage produced by the radiation.

In addition, it is believed that irradiation of the injury site with microbeam arrays advantageously assists in recovering the capillary blood vessels that are injured in a reversible manner. Segments of the endothelial cells in the direct path of the microbeams are destroyed (as would occur with conventional broad beams), but are regenerated by endothelial cells and vessel wall cells surviving between microbeams. Consequently, the massive vascular collapse and tissue collapse that occurs with conventional broad-beam treatment of spinal cord and brain injuries is avoided, and the tissue's microstructure, which is mainly the capillary blood vessels, is spared.

Specifically, in the prior art broad-beam methods for treating brain and spinal cord injury, the width of a conventional broad beam is too large to allow the above recovery process to proceed. Because the capillary blood vessels constitute the basic infrastructure of the tissue, its survival is the most important factor in the recovery of the entire CNS tissue from microbeam arrays.

The method of the present invention is also believed to advantageously promote the restoration of the "in-beam" glial cells and myelin in the healthy CNS tissue just outside the injury site, which are damaged by direct irradiation as the microbeams traverse a path to the injury site. For example, although the microbeams of the present invention can kill progenitor and mature glial cells and destroy myelin in the path of the individual beams, this system component also recovers, this time from the endogenous progenitor glial cells in the CNS tissue which survive between microbeams. These surviving cells migrate to the neighboring areas of direct exposure to microbeams in which the tissue has been depleted of glial cells. The cells then differentiate and become mature and functioning glial cells, including mature and myelinating oligodendrocytes. Finally, a remyelination process begins whereby lost myelin is replaced with a new, functioning myelin.

The microbeam array essentially "cleans" the gliosis produced at the injury site by reactive astrocytes, which forms the junction between healthy tissue, by using an adequately high dose, or "therapeutic dose" of X-ray radiation. The therapeutic dose as used herein is the in-beam, in-depth (at the depth of the injury) radiation dose, typically measured in units of Gray ("Gy"), required at the injury site to allow the damaged spinal cord or brain to recover from the injury. The therapeutic dose must, however, remain below the threshold for inducing permanent radiation damage to normal tissue in the beam path.

Preferably, the therapeutic dose of irradiation kills the glial cells in the path of the microbeams, mostly reactive astrocytes whose aggregation will (or has) produced the gliotic barrier, without damaging the cord itself. It is believed that the net effect is that the microvasculature at the junction reestablishes itself and the bridging process at the junction proceeds, leading to the rejoining of axons, functional remyelination and, consequently, functional restoration within the damaged spinal cord or brain. Basically, the microbeams are used to clean an injured area temporarily of inhibitors of regeneration by ridding the zone of reactive astrocytes, leukocytes and axon-growth inhibiting molecules such as CSPGs and KSPGs. Previous methods of broad-beam irradiation required low tolerable doses of irradiation to prevent radiation damage to normal tissue. These low doses are not capable of substantially assisting recovery of the injury site by, for example, cleaning an area entirely of reactive astrocytes, leukocytes and CSPGs/KSPGs.

The therapeutic dose, therefore, is preferably the dose required to substantially cleanse or remove the regeneration inhibitors, e.g., the reactive astrocytes, CSPGs, and KSPGs, at least temporarily, from the irradiated in-beam portion of the injury site.

Referring again to FIG. 1, in the method of the present invention, an injury site 10 of a portion of a nervous system, for example, the spinal cord 14, of a patient is irradiated through surrounding bone and tissue 15 with at least one array of microbeams 12. The array 12 includes at least two parallel, spatially distinct microbeams 16. The number and spatial arrangement of the microbeams in the array 12 are so chosen to deliver a therapeutic dose of X-ray radiation to the injury site 10 through the microbeams 16.

As indicated in FIG. 1, the injury site 10 as used herein refers to a volume targeted for irradiation treatment, which encompasses the tissue affected by the acute or chronic injury in addition to a marginal volume around the affected or damaged tissue. The marginal volume is determined by factors known to those skilled in the art of conventional radiation treatment. Such factors include the accuracy of the radiation source used in hitting a designated volume, and considerations of possible spreading or misestimation of the extent of tissue affected by the acute or chronic injury.

Figure 2:
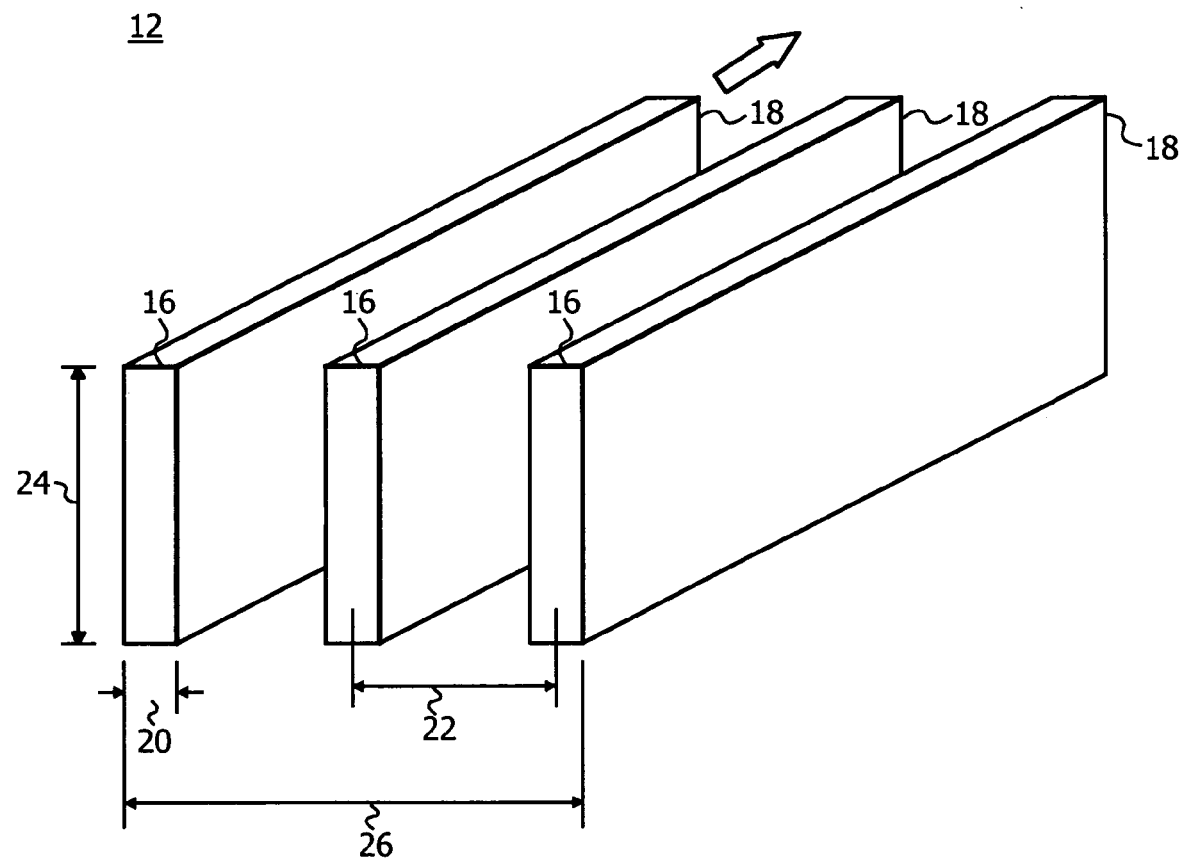
FIG. 2 is a magnified perspective representation of part of the microbeam array of FIG. 1.

As shown in FIG. 2, the microbeams 16 in an array 12 preferably include parallel irradiation planes (vertically oriented in the embodiment shown in FIGS. 1-4, but could also be horizontal or slanted) 18, and may also be referred to as microplanar beams 16. These microplanar beams 16 preferably have a substantially rectangular cross-section, with a beam thickness 20 corresponding to the short side of the rectangular cross-section. The array 12 is also characterized by a center-to-center beam spacing 22 and a width 24.

The term "beam spacing" as used herein refers to the center-to-center beam spacing 22, which is generally measured as the distance between the maximum intensity profile points of adjacent microbeams. In the case of a flat intensity dose profile in each microbeam, the center-to-center beam spacing 22 would be measured as the distance between the mid-points of the intensity profiles of adjacent microbeams.

In addition, the microbeams 16 generated in the array 12 are preferably substantially collimated at least in the plane perpendicular to the radiation plane, so that the spacing 22 is substantially maintained between the beams 16 as they traverse the subject. The microbeams 16 preferably also include substantially sharp, well-defined edges separating adjacent microbeams in the array 14, for sharp dose fall-off, thus minimizing the valley dose between the beams 16.

Preferably, the width 24 of the microbeams and a total length 26 of the array 12 are large enough to irradiate the entire volume enclosing the injury site 10, which includes some additional margin. A typical size of the microbeam array may be about 4 cm wide across a vertical spinal column, e.g., and 6 cm high along the vertical spinal column.

If the injury site 10, represented by a circle around a narrow horizontal line representing the location of a center of the injured tissue in FIG. 1, covers a height greater than that (width 24) of the microbeam array, however, then the therapeutic dose may be provided over the entire height of the injury site by translating the patient in the path of the at least two microbeams of the microbeam array (vertically, in FIG. 1). The method may include using a stepwise scanning method (step-and-shoot) in which the subject or source is translated in the beam at a certain step height after each irradiation step or in a continuously scanning method in which the subject or source is translated continuously. Similarly, if the extent 26 of the array 12 does not cover the injury site 10, arrays may be generated side-by-side using a stepwise scanning method.

Although the microplanar beam geometry described supra is preferred, any microbeam and microbeam array geometry capable of safely and effectively delivering the therapeutic dose and assisting recovery of the injury site are within the scope of the invention. For example, an array of cylindrical pencil beams may be used. In addition, the array may be a two-dimensional array, for example, a rectangular array of microbeams, the microbeams of the array being preferably substantially equally spaced. A rectangular or other two-dimensional array may be preferred when the cross-sections of the microbeams are circular, square, or otherwise substantially radially symmetrical.

Preferably, the microplanar beams 16 of the array 12 of the present invention are produced simultaneously using a multislit collimator having any of various designs known in the art. Such collimators have multiple radiation transmissive apertures that allow an array of spatially distinct microbeams to be simultaneously produced from a single wide radiation beam.

The multislit collimator generating the array 12 is preferably positioned in front of the X-ray source, but very close to the subject's body, in order to minimize the so-called "penumbra" or shadow of the source beam. Placing the collimator close to the beam, therefore, helps maintain the desirable sharp edges of the beams 16 throughout the subject.

The single X-ray radiation beam impinging on the multislit collimator may be generated by any source of X-rays capable of producing the required therapeutic dose. For example, the appropriate X-ray radiation may be generated by filtering radiation produced by a high energy synchrotron or an X-ray tube (bremsstrahlung radiation). The fluence rate of the source used to implement the method of the present invention is preferably high, so that exposure times are sufficiently short, reducing the possibility of smearing the microbeam dose pattern produced at the injury site.

One possible source of X-rays is a wiggler insertion device in a so-called "beamline" of a high-energy electron storage ring of an X-ray synchrotron. An exemplary beam source is the superconducting wiggler insertion device of the X17B beamline of the National Synchrotron Light Source at Brookhaven National Laboratory, Upton, N.Y. A conventional "planar" wiggler uses periodic transverse magnetic fields to produce a beam of rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam.

In a preferred embodiment, the source will be a bremsstrahlung X-ray generator. The bremsstrahlung X-ray source may include a high-throughput rotating anode X-ray tube operating at a very high voltage (preferably about 150 kV-peak or higher) and a very high current (100 mA or higher).

Whether the source is a bremsstrahlung source or storage ring, the beam is preferably filtered with copper or heavier elements to eliminate the low end of the energy spectrum, thus producing a higher mean spectral energy. Preferably, the half-power energy of the filtered X-ray beam is in the range of 100-250 keV. For example, to produce the desired energy spectrum from a high-throughput rotating anode tube operating at 140-250 kVp, the beam should be heavily filtered, e.g., through about 1-10 mm thick copper.

Most preferably, the X-ray source is one or more X-ray tubes generating bremsstrahlung radiation. One X-ray tube may be used and either the subject or the tube repositioned to produce the microbeam arrays of the present invention. Alternatively, multiple X-ray tubes may be maintained in fixed positions arranged around the patient, at the appropriate angles of incidence to the patient, to generate the arrays in accordance with the methods of the present invention.

The focal spot size of the X-ray tube(s) should be minimized to reduce the beam penumbra, assuring sharp edges and thus a sharp dose fall-off to minimize the valley dose. Optimally, X-ray tubes for use with the method of the present invention include a) a source spot size smaller or comparable to the thickness of the microplanar beams, b) a stable stand to keep the tube fixed at different angles with little vibrations, and c) a geometry that allows placement of the tube close to the subject (preferably within 50 centimeters), in order to maximize the dose rate.

Referring again to FIG. 2, the optimal beam thickness 20 and spacing 22 will vary depending on the characteristics of the source. The ratio of beam thickness 20 to center-to-center beam spacing 22, however, will preferably be in a range of from about 1 to 4 to about 1 to 16, regardless of whether the source is a high-energy electron storage ring or a bremsstrahlung X-ray tube.

In one embodiment, the ratio of thickness 20 to center-to-center beam spacing 22 is in a range from about 1 to 6 to about 1 to 8.

In another embodiment, the ratio of beam thickness 20 to center-to-center beam spacing 22 will be substantially equal to 1 to 7.

If a synchrotron source is used to generate the microbeams and implement the method of the present invention, for example, one preferable choice of beam thickness 20 and spacing 22 are 30 micrometers ($\mu$m) and 210 $\mu$m, respectively (1:7). If a bremsstrahlung X-ray tube is used, a more preferable choice is a beam thickness 20 of about 0.7 mm (or within a range of about 0.5 mm to 0.9 mm) and beam spacing of about 4.9 mm (or within a range of about 3.5 mm to 6.3 mm). Though a larger beam size is preferred when using an X-ray tube, the same ratio of thickness 20 to spacing 22 of 1 to 7 as the synchrotron-beam example is preferred.

The preferred thickness of the microbeams for implementing the method of the present invention using a bremsstrahlung source is larger, because the effective source spot size in bremsstrahlung sources is larger than that of a storage ring. The effective source spot size is defined as the angle at which the source spot size is viewed from the position of the target, or, equivalently, the ratio of the source size to the distance between the source and the target. Although the actual spot sizes in the synchrotron and the bremsstrahlung sources might be comparable to each other, the source-to-target distance is much larger for the synchrotron source (about 10 m) than for the bremsstrahlung source (about 1 m).

In a preferred embodiment, therefore, the method includes providing the microbeam array of X-ray radiation using a bremsstrahlung radiation source, e.g., X-ray tubes, where the thickness of the microbeams is substantially in a range of about 0.1 mm to 1.0 mm. In addition, the ratio of beam thickness 20 to center-to-center beam spacing 22 is preferably substantially equal to 1 to 7.

In another embodiment, the beam thickness 20 is substantially equal to or greater than about 0.02 mm (20 $\mu$m) and less than or equal to about 1.0 mm.

In still another embodiment, preferably using synchrotron X-ray radiation, the beam thickness is substantially equal to or greater than about 20 $\mu$m and less than or equal to about 100 $\mu$m.

In yet another embodiment, microbeams are provided which include a width substantially less than or equal to about one millimeter.

The therapeutic dose of the present invention to allow substantial recovery of the brain or spinal cord from the injury is preferably within a range of about 30 to about 500 Gy in-beam in-depth dose, where the in-beam in-depth dose refers to the dose inside each microplanar beam at the depth, within the body, of the spinal cord or brain.

It is well known to those skilled in the art that the threshold dose, or maximum tolerable dose before neurological and other complications of radiotherapy arise, increases as irradiated volumes of tissue are made smaller. Equivalently, as the irradiated volume (beam thickness) increases, the maximum tolerable dose decreases. The beam thickness, therefore, partially sets the upper limit of the therapeutic dose that can be safely administered.

In the preferred embodiment of the present method, a bremsstrahlung source is used to deliver the therapeutic dose. As discussed supra, the thickness of the microbeams produced will then preferably be in a range of about 0.5 mm to about 0.7 mm with a ratio thickness to beam spacing of about 1:7. The therapeutic dose for this case is then limited to a smaller upper limit. In one embodiment, the in-beam, in-depth dose is preferably within a range of about 30 to about 200 Gy.

The required rate at which the dose is delivered, i.e., the dose rate, depends on the dose to be administered. If the in-beam dose required is about 100 Gy, then the dose rate should be at least about 2 Gy per minute to allow administration of the 100 Gy dose in about 50 minutes. Both types of sources are capable of this dose rate. In general, however, a synchrotron source can provide a much higher dose rate than X-ray tubes.

The injury site may be irradiated, according to the present invention, within 20 days or less after the injury occurred, i.e., while the injury is still classified as an acute injury The injury site may also be irradiated 20 days after the injury to assist recovery of a chronic injury.

In addition, the therapeutic dose may be delivered either in a single session (single dose fraction) or in several sessions in so-called "dose fractions" or "dose fractionations" separated by a time interval. As referred to herein, however, the dose fractions are defined in the same way as the therapeutic dose: each dose fraction includes the in-beam in-depth therapeutic dose required at the injury site to allow the damaged spinal cord or brain to substantially recover from the injury.

In other words, the transient damage to the irradiated portion of the injury site is sufficient, in every session, to allow that portion to be at least temporarily cleaned of regeneration inhibitors, so that neighboring progenitor glial cells can migrate to the injured portion and begin a process of repair.

The in-beam tissue dose (i.e., in-depth dose) in all fractions must be high enough to ablate the target cells, such as progenitor glial cells or reactive astrocytes; i.e., the same as the in-beam in-depth therapeutic dose. Therefore, no matter how many dose fractions are used, each dose fraction must be above the cell-ablation threshold, and is not accumulative. In this sense, the term "dose fraction" is simply the in-beam in-depth therapeutic dose required, and not a fraction thereof. However, the "valley" dose, which is accumulative, must be kept as low as possible (through the optimal choice of the beam width, beam spacing, and the in-beam dose). Here the limitation is that the accumulative valley dose for the entire treatment period will not surpass the limit of tissue tolerance for dose-fractionated broad beams in the same fractionation schedule.

In a preferred embodiment, several dose fractions, i.e., therapeutic doses, are administered to the subject by irradiating the injury site in subsequent sessions from different angles with so-called "angle-variable intersecting microbeam arrays ("AVIMA").

By applying dose fractionation with AVIMA, normal tissue in the path of the beam is irradiated only once, thus minimizing possible radiation damage to normal tissue. In addition, regions of the injury site receiving multiple in-beam in-depth therapeutic doses, receive a higher summed dose to more effectively clean the gliotic tissue. Another advantage of the AVIMA geometry, as described below, is that a greater area of the injury site is irradiated.

Referring again to FIG. 3, in an embodiment of a method of the present invention, therefore, a therapeutic dose is administered in more than one session using angle-variable intersecting microbeam arrays. The microbeam arrays intersect substantially only at the injury site 10, as indicated by the grid-like regions of intersection 28 in FIG. 3 within the area of the injury site 10. The method using AVIMA preferably includes irradiating the injury site 10 with arrays of angle-variable microbeams centered around and including a "zero angle" array 30. Preferably, the zero angle array 30 is directed to squarely impinge on the subject's back, i.e., the array 30 is normally incident (90 degree angle of incidence) on the back. Adjacent angle-variable intersecting arrays (34, 30) are separated by an angular displacement 32. A first therapeutic dose is delivered in one of the angle-variable microbeam arrays 30 at "Time Zero" on Day 1 of treatment during a first session.

The method further includes angularly displacing by a non-zero integer multiple of the displacement angle 32 either the X-ray source or the subject about an axis of rotation 35 through a center of the injury site 10 (See FIG. 1) and, after a time interval between sessions, additionally irradiating the injury site 10 with one of the angularly displaced, i.e., angle-variable intersecting microbeam arrays 34. The axis of rotation 35 is preferably substantially parallel to the irradiation planes 18 of the microbeams 16 (see FIGS. 1-2). The method includes repeatedly angularly displacing and additionally irradiating after the time interval, until the injury site 10 has been irradiated a total number n of times over n sessions separated by the time interval, by a total number n of AVIMAs.

In another embodiment, the number of irradiations may also be doubled by reirradiating a second time at each angular position of each angle-variable array using a second irradiation geometry. The second irradiation geometry is provided by either reorienting the multislit collimator provided between the source and the subject, or by changing to a different collimator. The two different positions may include different slanted orientations (not horizontal or vertical), horizontal, or vertical orientation. The method described supra of administering angle-variable intersecting arrays, wherein each array comprises a therapeutic dose of radiation would then be repeated. When the irradiation geometry is described by vertically-oriented microbeams, the subject or source is rotated by some multiple of the angular displacement angle 32 from one fraction to the next (for different AVIMAs) about a vertical axis centered through the injury site. When the irradiation geometry is described by horizontally-oriented microbeams, the subject or source is rotated about a horizontal axis. When slanted microbeams are used, the angle of rotation or displacement is parallel to the slanted axis. Though a temporal sequence of sessions may alternate randomly in both irradiation geometry (orientation of the irradiation planes) and angular displacement, it is probably more practical to first irradiate the injury site at all angles of the AVIMAs using one irradiation geometry before turning/changing the collimator (or subject) to a second irradiation geometry.

In one embodiment, every angle-variable intersecting microbeam array irradiating the injury site can have a different irradiation orientation.

The following further describes the most likely geometries of the irradiations, although not the only ones, given the practicality of implementing the present method with existing X-ray sources. The microbeam arrays may be propagated horizontally from a source, which would be the case for most synchrotron beams and some X-ray tubes. Optionally, the arrays may be propagated vertically from a source pointing up from the floor or down from the ceiling (most X-ray tubes beam).

Horizontal beams will preferably be administered with the patient either sitting upright on a patient positioning chair, or lying down on his/her side on a patient positioning bed. Vertical beams will preferably be used with the patient lying down on the bed other on his/her back (with the beam coming up from the floor), or lying down on the bad on his/her front (with the beam coming down from the ceiling). For both the horizontally and vertically propagating beams, the patient's back is toward the beam and the angle of incidence of the microbeams in the array is 90 degrees for the "zero angle" of irradiation. The additional arrays are preferably centered around the zero angle array. In the discussion that follows the "Time Zero" or first dose fraction is at the zero angle. Subsequent irradiation angles may vary widely for different dose-fraction administration. The parallel irradiation planes of the individual microbeams in an array are preferably aligned either vertically or horizontally, at least in the geometry of "zero angle." However, the alignment angle may be titled for other irradiation geometries as discussed above, by repositioning the subject or the collimator in front of the X-ray source generating the arrays. In other words, the irradiation geometry may be different for every dose fraction administration for every angle-variable intersecting microbeam array.

Figure 3:
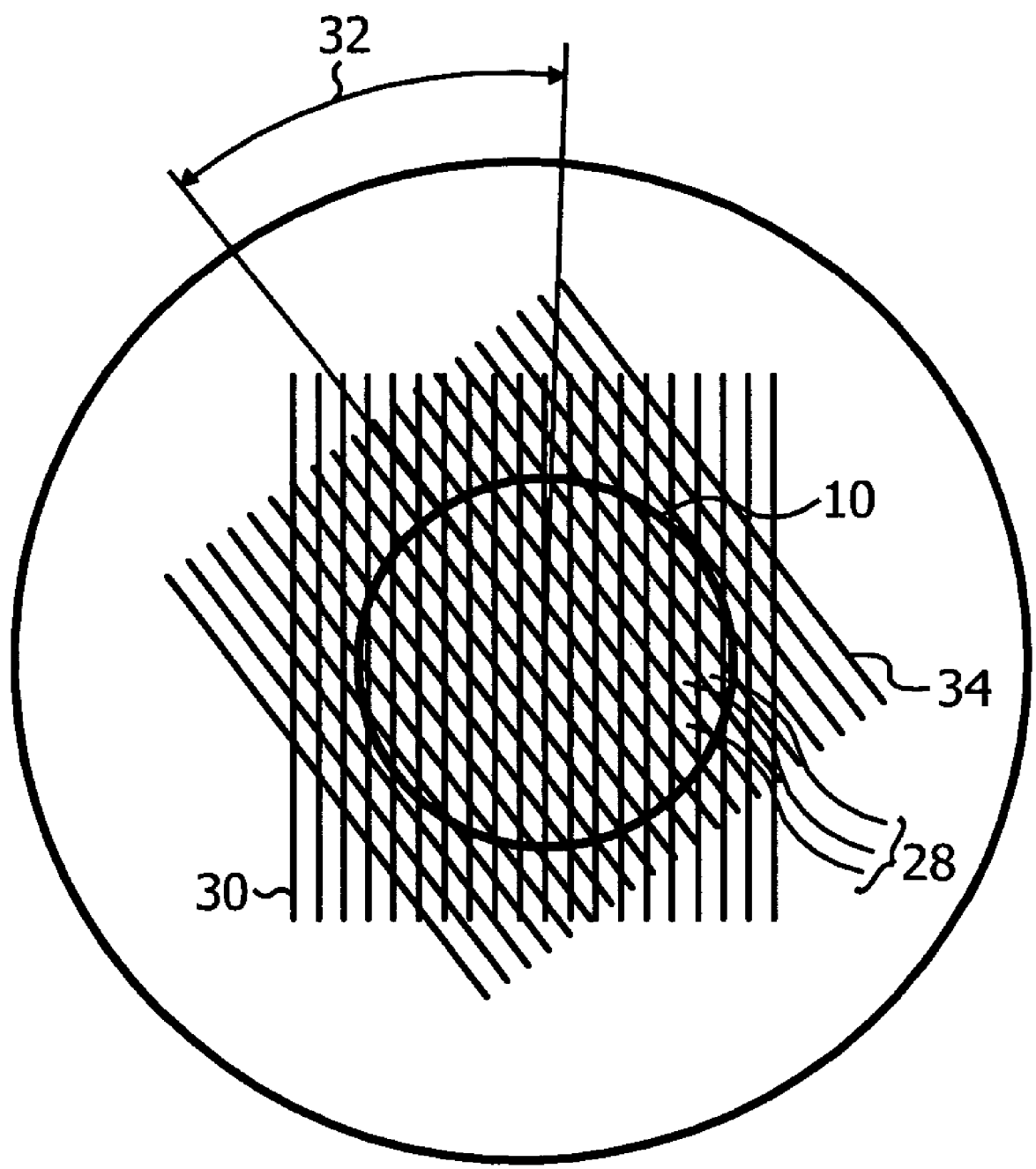
FIG. 3 is a top cross-section view through the injury site of FIG. 1, including a schematic representation of two angularly displaced exposures of the injured spinal cord with the microbeam array in accordance with an embodiment of a method of the present invention.

Referring to FIGS. 1-4, the following example describes the angle-changing geometry. In this example, the beam array 12 propagates horizontally, the X-ray source irradiating the injury site 10 from the side. The microplanar beams 16 in the array are vertical, and the patient sits upright (spinal cord 14 vertical) with the back to the beam for the zero angle geometry (first fraction). The incident angle of the beam 12 on the subject between the dose fractions will then change laterally, as shown in FIG. 3. In other words, either the source or the subject rotates around a vertical axis that goes through the center of the injury site 10 in the patient's spinal cord 14 between dose fractions.

AVIMA with dose fractionation may be implemented similarly in any combination/orientation of the beam and patient geometries. For example, in the above example (horizontally propagating beam; upright or on-the-side patient) one can also use horizontally oriented microplanar beams instead of vertically oriented ones (in the zero angle geometry), and rotate the source or the patient about a horizontal axis that goes through the injury site (although the beam can be rotated only when produced by an X-ray tube).

Not all combinations of the motions, however, are possible. For example, for vertically propagating beams (patient lying on his/her back or front) there will be two possible orientations of the parallel irradiation planes 18 of the microplanar beams 16: either parallel to the spinal cord or perpendicular to it. If parallel, then the source or patient should be rotated about the spinal cord between dose fractions, while, if perpendicular, the rotation should be about a horizontal axis perpendicular to the spinal cord. In both these cases it will not be easy to rotate the patient because his/her general positioning may change, thus the rotation is preferably implemented by rotating the source.

Several dose fractions (sessions), may be administered using AVIMA, preferably ranging from a total of about 3-30, using one or more of the irradiation geometries of the microplanar beams described above. For example, in the example using a horizontally propagating beam and patient sitting upright or lying on his/her side (side-reclined position), the therapeutic dose can be given at each angle corresponding to the AVIMAs once with horizontally oriented microplanar beams and once with vertically oriented ones. Each session is separated by a minimum time interval.

In one embodiment, the minimal time between sessions in which each dose fraction is administered is at least about six (6) hours.

In another embodiment, the time between sessions preferably ranges from about twelve (12) hours to about thirty-six (36) hours.

In yet another embodiment, the time between sessions preferably ranges from about twelve (12) hours to about seven (7) days.

Retreatment of chronic spinal cord injury is also within the scope of the method of the present invention. The entire treatment is preferably repeated, if needed, within about six (6) to eighteen (18) months after a previous treatment.

A further illustration of the AVIMA method of the present invention includes the preferred geometry of the microbeam arrays of the present invention, for which the beam thickness is about 1/7 of the center-to-center beam spacing. In each dose fraction, therefore, about 14.3% of the target's volume is irradiated. If the dose is adequately high to kill all progenitor glial cells residing in the direct beam path, 14.3% of the entire population of such cells are ablated in the first dose faction administration. The additional percentage of progenitor cells in subsequent fractions, preferably administered at wide angles to the direction of the first or "zero angle" beam, is slightly smaller than this number, due to the geometry. The microbeams of the angularly displaced arrays will intersect a subregion of the zero angle-irradiated regions of the injury site. In other words, smaller areas of the array from one dose fraction will cross those from an earlier fraction. In general, if the letter "r" denotes the ratio of beam width divided by beam spacing, and letter "n" denotes the number of dose fractions, the surviving fraction "s" of the directly-hit progenitor glial cells after n dose fractions is defined by equation (1) to be:

$$s=1-(1-r)^n \quad (1)$$

Therefore, for r=0.143 (1:7 thickness to spacing ratio) and n=5 dose fractions (sessions), one finds s=0.54, i.e., about 54% of the cells will be hit directly at least once. If each directly-hit progenitor leads to a rejuvenated, mature glial cell, then about 54% of the glial system will be rejuvenated in this example.

If two sets of irradiations are carried out using two different irradiation geometries, at each of n angular positions of the angle-variable intersecting microbeam arrays, then 2n dose fractions are administered over 2n sessions, and $s=1-(1-r)^{2n}$.

Figure 4:
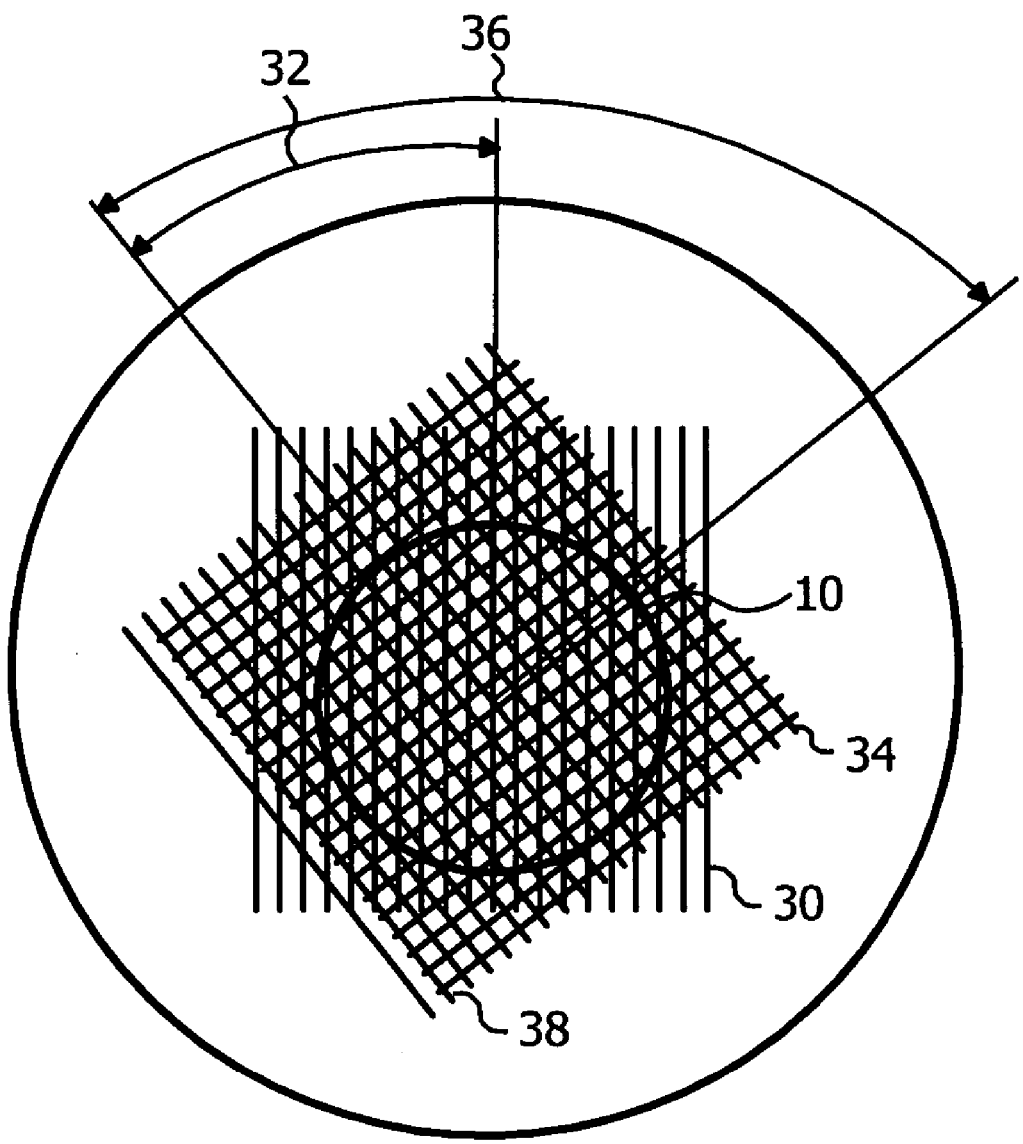
FIG. 4 is a top cross-section view through the injury site of FIG. 1, including a schematic representation of three angularly displaced exposures of the injured spinal cord with the microbeam array in accordance with an embodiment of a method of the present invention.

Referring to FIG. 4, in dose-fraction with AVIMA, the administration angles for different dose fractions are chosen to provide the widest possible angular spread θ 36 among the fractions. The angular spread 36 encompasses all of the angle-variable intersecting microbeam arrays. The maximum spread 36 is limited to the angular access afforded by the location of the injury, patient-positioning ability of the equipment and the irradiation source. Because the irradiation is administered to the back, less than 180° of angular spread will be available. A reasonable variation is probably about 140° angular spread θ36 for each possible angle variation geometry, i.e., from zero angle in which the patient's back is precisely facing to beam, to ±70°.

In one embodiment, the angular spread 36 is substantially in a range between about 130 degrees to about 150 degrees.

In general, the formula to choose the angular spacing between the beams for n dose fractions or sessions is preferably equal to θ/(n−1). For example, for n=3 (three fractions only), and θ=140°, the angular displacement will be 70° between irradiations, and the angles will be −70°, 0°, and +70°, where 0° represents the angle at which the beams hit the patient's back. Similarly, for n=5, the microbeam array is angularly displaced by about 35° between irradiations; thus the angles will be −70°, −35°, 0°, +35°, and +70°. As indicated supra, these dose fractions can also be divided into two groups per session, using different irradiation geometries or orientations of the microplanar beams, thus increasing further the angular range between fractions.

The choice of the orientation of the microplanar beams with respect to the spinal cord may have physiological/neurological consequences for two reasons. First, the spinal cord is essentially made of long axons either coming from the brain or returning to the brain. Second, the breathing cycle of the patient may cause the spinal cord to move up and down or sideways, a motion which may smear the dose distribution of the microbeam array.

In general, it may be safer to have the microplanar beams not parallel to the cord because they may engulf long segments of axons. This consideration might be more important when used wider microbeams (e.g., 0.7 mm wide). The breathing motion should also be taken into account, however, which is more important for microbeam arrays with small beam width and small beam spacing. For example, for a horizontally propagating beam with the patient sitting upright with his/her back to the beam, it might be advantageous to use horizontally oriented microplanar beams than vertical ones not to be parallel to the cord, although in this geometry an array with horizontal microplanar beams may be more vulnerable to beam smearing because the breathing motion may be more an up-and-down one.

Preferably, the method of the present invention includes maximizing removal of the substantial amount of regeneration inhibitors from the portion of the injury site by optimizing several factors, such as the therapeutic dose of a single fraction, and minimizing the valley dose to minimize damage to the adjacent tissue between the microbeams. The in-beam in-depth therapeutic dose to valley dose ratio may be also optimized by controlling at least one of the thickness of the microbeams, the spacing between microbeams, the ratio of the thickness to the spacing, and the energy spectrum of the microbeam array.

In order to optimize the in-beam therapeutic dose to valley dose or "peak-to-valley" ratio, the dose fall-off at the edge of any individual microbeam inside a microbeam array of the present invention is preferably sharp enough at beam energies of between about 50 keV and about 200 keV, and at tissue depths of from about 1 cm to about 40 cm, to result in large peak-to-valley dose ratios for the present invention. Such large ratios allow dose planning so that the peak dose will be lethal to the regeneration inhibitors such as reactive astrocytes and axon-growth inhibiting molecules of CSPGs and/or KSPGs, while valley doses will be low enough to allow most normal and regenerative cells, such as progenitor glial cells, to survive the radiation. These glial cells can then migrate to the cleansed irradiated portion of the injured site to assist in tissue repair.

The appropriate selection of the parameters of microbeam field configuration and peak dose is critical to the efficacy of microbeam radiation therapy for assisting recovery of damaged nervous system such as the brain and spine. The peak dose along the microbeam axis and the center-to-center spacings of the microbeams must be appropriately selected to ensure sufficiently low doses to tissue present in the valleys between the microbeams. The implemented combination of dose and configuration allows endothelial cells, oligodendrocytes (in brain tissue), and glial cells between the microbeams to divide and to repopulate the irradiated portion of the injured site, as well as the in-beam tissues damaged by the radiation treatment outside the injury site. Thus, unidirectional exposure does not permanently damage normal tissue.

In one embodiment, a therapeutic in-beam in-depth dose is delivered in fractionated doses in a range from about 30 Gy to about 500 Gy. The number of fractionated doses is preferably in a range of about 3 to 30 doses.

The success of the AVIMA methods of the present invention relies in part, therefore, on maintaining accurate microbeam placement from session to session, and during the exposure time of one session. Therefore, the methods of the present invention are preferably implemented using stereotactic apparatus to preferably eliminate or at least substantially minimize so-called macromotion, for example, from random movements of the patient.

Other sources of motion, referred to as tissue "micromotion" as discussed supra are induced by physiomechanical cycles, namely, cardiac pulsations and pulmonary or respiratory cycles. The methods of the present invention may, therefore, be performed in a pulsed mode, the pulsations of the microbeams being synchronized with the subsequent rhythmic displacements of the injury site. Most preferably, the pulses are synchronized with an electrocardiogram, as described, for example, in the Slatkin, et al. patent.

In one embodiment of the present invention, the high energy electromagnetic radiation source is pulsed, so that the microbeam array is delivered in a plurality of temporally discrete pulses. Preferably, the temporally discrete pulses are substantially synchronized with a physiomechanical cycle of the patient. Most preferably, the physiomechanical cycle includes at least one of a cardiac cycle and a cardiopulmonary cycle.

In another embodiment of the present invention, a method of the present invention includes combining the microbeam irradiation of the injury site using any of the beam geometries and characteristics discussed herein with transplantation of embryonic stem (ES) cells to the injury site. It is believed that the combination of these two methods will greatly enhance the recovery of an injury to a portion of a nervous system, particularly, to the brain or spinal cord.

It is very much likely that the population of endogenous glial stem cells naturally existing in the spinal cord (also called progenitor glial cells), once stimulated by microbeam irradiations to proliferate and differentiate, will be adequate to complete the process of the "glial system rejuvenation" which may be necessary to allow axonal growth and reconnection, as well as remyelination toward the recovery from spinal cord injury. However, it is also possible that external administration of stem cell will assist the recovery process by accelerating it or by making it more efficient. The administered stem cells might be human or animal embryonic cells. The stem cell administration may or may not require a surgical process.

The methods of the present invention may be used to treat both acute cases of spinal cord or brain injuries, existing for up to 20 days after injury, and chronic cases of spinal cord injuries, which are older than 20 days.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

The invention claimed is:

1. A method of assisting recovery of an injury site of an acute or chronic injury to a brain or spinal cord of a subject, the method comprising: irradiating the injury site with at least one array of microbeams comprising at least two parallel, spatially distinct microbeams in an amount and spatially arranged to deliver a therapeutic dose of X-ray radiation to said injury site, said therapeutic dose of X-ray radiation inhibiting the formation of a scar barrier and simultaneously promoting the regeneration of a microvascular and glial system at said injury site.

2. The method of claim 1, wherein said irradiating further comprises delivering the therapeutic dose with the at least one array of microbeams to the injury site repeatedly in a number n of sessions, each session being separated by a time interval.

3. The method of claim 2, wherein the at least one array comprises a number n of angle-variable intersecting microbeam arrays, the method further comprising generating the angle-variable intersecting microbeam arrays.

4. The method of claim 3, wherein said generating comprises the steps of:
irradiating the injury site with one of the angle-variable intersecting microbeam arrays in one session;
angularly displacing at least one of an X-ray radiation source generating the at least one array and the subject about an axis of rotation through a center of the injury site, wherein the axis of rotation is parallel to the at least two parallel, spatially distinct microbeams, to produce a second one of the angle-variable intersecting microbeam arrays;
additionally irradiating the injury site with the second one of the angle-variable intersecting microbeam arrays after the time interval in a second session; and repeating said angularly displacing and additionally irradiating a number (n−1) times to generate the number n of angle-variable intersecting microbeam arrays, wherein the number n of angle-variable intersecting microbeam arrays intersect substantially only within the injury site, the injury site including a marginal volume surrounding injured tissue.

5. The method of claim 4, wherein adjacent angle-variable intersecting arrays are separated by a displacement angle, said angularly displacing comprising angularly displacing by a non-zero integer multiple of the displacement angle.

6. The method of claim 5, wherein the displacement angle is substantially equal to $\theta/(n-1)$, wherein $\theta$ is predetermined by an angular access of an X-ray source generating the angle-variable intersecting microbeam arrays to the injury site, $\theta$ being a total angular spread encompassing the angle-variable intersecting microbeam arrays.

7. The method of claim 6, wherein $\theta$ is substantially in a range of about 130 degrees to about 150 degrees.

8. The method of claim 3, wherein said generating comprises generating the angle-variable intersecting microbeam arrays for one of a horizontal, vertical, and slanted irradiation orientation of the at least two parallel, spatially distinct microbeams.

9. The method of claim 8, further comprising additionally generating a second number n of angle-variable intersecting microbeams arrays for another one of a horizontal, vertical and slanted irradiation orientation of the at least two parallel, spatially distinct microbeams, for a total number 2n of sessions, each session being separated by the time interval.

10. The method of claim 9, said additionally generating further comprising one of reorientating and replacing a multislit collimator between an X-ray source and the subject to change the irradiation orientation.

11. The method of claim 9, wherein the total number 2n of sessions is within a range of from three (3) to thirty (30) sessions.

12. The method of claim 2, wherein the time interval is substantially within a range of from about twelve (12) hours to about seven (7) days.

13. The method of claim 1, wherein the subject is positioned in one of an upright position, a side-reclined, and a slanted position, and wherein the at least one array is directed onto a subject's back, the at least one array being centered around a 90-degree angle of incidence.

14. The method of claim 1, wherein the at least one array comprises a center-to-center spacing between adjacent microbeams and a thickness of each of the at least two parallel, spatially distinct microbeams, wherein a ratio of the center-to-center spacing to the thickness is substantially in a range of about 4 to about 16.

15. The method of claim 1, wherein each of the at least two parallel, spatially distinct microbeams comprise a thickness substantially in a range of from about 0.02 mm to 1.0 mm.

16. The method of claim 1, wherein said irradiating further comprises generating said X-ray radiation with an X-ray bremsstrahlung source.

17. The method of claim 16, wherein each of the at least two parallel, spatially distinct microbeams comprise a thickness substantially in a range of from about 0.1 millimeters to 1.0 millimeter.

18. The method of claim 1, wherein said irradiating comprises generating X-ray synchrotron radiation, each of the at least two parallel, spatially distinct microbeams comprising a beam thickness substantially in a range of about 20 micrometers to about 100 micrometers.

19. The method of claim 1, wherein said irradiating further comprises generating X-ray radiation having a filtered broad beam energy spectrum, a half-power energy being substantially in a range from at least about 100 keV to about 250 keV.

20. The method of claim 1, wherein the therapeutic dose comprises an in-beam in-depth dose in each microbeam substantially in a range from about 30 Gy to about 500 Gy.

21. The method of claim 1, further comprising delivering stem cells to the injury site.

22. The method of claim 1, said irradiating further comprising delivering said at least one array in a plurality of temporally discrete pulses of said X-ray radiation.

23. The method of claim 22, wherein the plurality of temporally discrete pulses are substantially synchronized with a physiomechanical cycle of the subject.

24. The method of claim 23, wherein the physiomechanical cycle comprises at least one of a cardiac cycle and a cardiopulmonary cycle.

* * * * *